(12) United States Patent
Tuan

(10) Patent No.: US 11,925,727 B2
(45) Date of Patent: Mar. 12, 2024

(54) INTERVERTEBRAL FUSION DEVICE

(71) Applicant: National Taiwan University, Taipei (TW)

(72) Inventor: Wei-Hsing Tuan, Taipei (TW)

(73) Assignee: National Taiwan University, Taipei (TW)

( * ) Notice: Subject to any disclaimer, the term of this patent is extended or adjusted under 35 U.S.C. 154(b) by 197 days.

(21) Appl. No.: 17/384,824

(22) Filed: Jul. 26, 2021

(65) Prior Publication Data
US 2022/0401623 A1    Dec. 22, 2022

(30) Foreign Application Priority Data

Jun. 18, 2021 (TW) ................... 110122315

(51) Int. Cl.
| | | |
|---|---|---|
| *A61F 2/44* | (2006.01) | |
| *A61L 27/06* | (2006.01) | |
| *A61L 27/10* | (2006.01) | |
| *A61L 27/38* | (2006.01) | |
| *A61L 27/40* | (2006.01) | |
| *A61L 27/56* | (2006.01) | |

(52) U.S. Cl.
CPC ........... *A61L 27/3856* (2013.01); *A61L 27/06* (2013.01); *A61L 27/105* (2013.01); *A61L 27/40* (2013.01); *A61L 27/56* (2013.01); *A61L 2430/38* (2013.01)

(58) Field of Classification Search
CPC ........ A61F 2/442; A61F 2/4455; A61F 2/446; A61F 2/4465; A61F 2/447
USPC ................. 623/17.11, 17.12, 17.16
See application file for complete search history.

(56) References Cited

U.S. PATENT DOCUMENTS

| | | |
|---|---|---|
| 8,052,787 B2 | 11/2011 | Tuan et al. |
| 8,123,812 B2 | 2/2012 | Khandkar |
| 8,263,513 B2 | 9/2012 | Tuan et al. |
| 8,579,978 B2 | 11/2013 | Marnay et al. |
| 8,906,817 B2 | 12/2014 | Tuan et al. |
| 10,741,176 B2 | 8/2020 | Canim et al. |
| 11,612,494 B2 * | 3/2023 | Mazur .................. A61F 2/4455 623/17.16 |

(Continued)

FOREIGN PATENT DOCUMENTS

| | | |
|---|---|---|
| CN | 100571658 | 12/2009 |
| CN | 112402070 | 2/2021 |

(Continued)

OTHER PUBLICATIONS

"Office Action of Taiwan Counterpart Application", dated Jul. 5, 2022, pp. 1-3.

(Continued)

*Primary Examiner* — Eduardo C Robert
*Assistant Examiner* — Christina Negrellirodriguez
(74) *Attorney, Agent, or Firm* — JCIPRNET

(57) ABSTRACT

An intervertebral fusion device includes a structural ceramic body. The structural ceramic body has a bottom surface, a top surface, a peripheral surface connected between the bottom surface and the top surface, and at least one pore channel penetrating the bottom surface and the top surface. The inner surface of the pore channel is either a convex curved surface or a funnel-shaped surface. For the pore channel having the convex curved surface, the pore diameter of the pore channel gradually expands from the center of the pore channel to the top surface and the bottom surface. The pore diameter can also gradually expand from the bottom surface to the top surface. The peripheral surface of the structural ceramic body is wavy or zigzag.

11 Claims, 8 Drawing Sheets

(56) References Cited

U.S. PATENT DOCUMENTS

| | | | |
|---|---|---|---|
| 2005/0049706 A1 | 3/2005 | Brodke et al. | |
| 2005/0246021 A1* | 11/2005 | Ringeisen | A61B 17/846 606/76 |
| 2012/0179261 A1 | 7/2012 | Soo | |
| 2012/0330420 A1 | 12/2012 | Brodke et al. | |
| 2013/0302512 A1 | 11/2013 | McEntire et al. | |
| 2015/0238321 A1 | 8/2015 | Pflum | |
| 2016/0106540 A1* | 4/2016 | Kuntz | A61F 2/2846 264/44 |
| 2016/0213488 A1* | 7/2016 | Moore | A61F 2/4465 |
| 2018/0256336 A1* | 9/2018 | Mueller | A61F 2/2846 |
| 2018/0280154 A1 | 10/2018 | Lewis et al. | |
| 2019/0183653 A1* | 6/2019 | Gregersen | A61F 2/447 |

FOREIGN PATENT DOCUMENTS

| | | |
|---|---|---|
| CN | 112603602 | 4/2021 |
| EP | 1504732 | 2/2005 |
| JP | 2005529634 | 10/2005 |
| JP | 2019519334 | 7/2019 |
| TW | 358733 | 5/1999 |
| TW | I380832 | 1/2013 |
| TW | I488828 | 6/2015 |
| TW | I650144 | 2/2019 |
| TW | I652075 | 3/2019 |
| TW | M597117 | 6/2020 |

OTHER PUBLICATIONS

C.L.Hsieh et al., "Elastic behaviour of a model two-phase material," Journal of the European Ceramic Society vol. 24, Issues 15-16, Dec. 2004, pp. 3789-3793.

"Office Action of Japan Counterpart Application", dated Jul. 10, 2023, p. 1-p. 5.

"Notice of Reasons for Refusal of Japan Counterpart Application No. 2022095465", dated Jan. 15, 2024, pp. 1-5.

* cited by examiner

INTERVERTEBRAL FUSION DEVICE

CROSS-REFERENCE TO RELATED APPLICATION

This application claims the priority benefit of Taiwan application serial no. 110122315, filed on Jun. 18, 2021. The entirety of the above-mentioned patent application is hereby incorporated by reference herein and made a part of this specification.

BACKGROUND

Technology Field

The disclosure relates to a device implanted between vertebrae, and particularly relates to an intervertebral fusion device with low stiffness but with uniform internal stress distribution.

Description of Related Art

The spine is the most important bones in a human body. The spine generally consists of 26 vertebrae, including 7 cervical vertebrae, 12 thoracic vertebrae, and 5 lumbar vertebrae. The spine, along with muscles and ligaments, provides support for the weight of the entire human body.

Intervertebral discs sit between the vertebrae of vertebrates. These intervertebral discs are relatively soft and provide lubrication for the sliding between the vertebrae of vertebrates. The sliding between the vertebrae of each vertebrate gradually results in the wear of the intervertebral discs, severely leading to the collapse or deformation of the intervertebral discs, then compressing the nerves, and causing pain. Therefore, implanting an intervertebral fusion cage between the vertebrae is one of the common methods to alleviate the suffering of patients.

Metal such as titanium alloy or stainless steel is one of the materials conventionally used for intervertebral fusion cages. However, stainless steel may release some toxic ions (e.g., nickel) into the blood system, so an intervertebral fusion cage made of titanium alloy is more commonly used in clinical practice. However, the elastic modulus of titanium alloy is about 114 GPa, which is greater than the elastic modulus of bone. To reduce the stiffness, generally, a large hole is disposed in the center of the titanium alloy intervertebral fusion cage, and the hole is a pore channel. The position of the pore channel can be filled with an autologous graft or a bone graft.

Although the stiffness of the titanium alloy intervertebral fusion cage has been reduced through a central pore channel, the problem of the intervertebral cage subsidence still occurs after a period of transplantation because all the stresses are concentrated on the edge of the titanium alloy intervertebral fusion cage. Moreover, titanium alloy is a metal material and interacts with electromagnetic waves, so when X-rays, magnetic resonance imaging (MRI) scans, and computed tomography (CT) scans are adopted to observe the implanted titanium alloy intervertebral fusion cage, the images around the fusion cage are blurred, resulting in difficulty in postoperative observation.

Another polymer intervertebral fusion cage has also been developed. The material of the polymer intervertebral fusion cage is usually polymethylmethacrylate (PMMA) or polyetheretherketone (PEEK). The elastic modulus of PEEK is about 5 GPa, which is close to the stiffness of bones. PEEK is also very strong. However, PMMA and PEEK are made by polymerizing monomers, and a small number of toxic monomers are released into the human body after a long period of time.

Therefore, the intervertebral fusion cages still require the followings in clinical practice:
1. The stiffness of the intervertebral fusion cage matches the stiffness of the vertebrae in the vicinity;
2. The intervertebral fusion cage is strong enough to support the body weight;
3. A pore channel is required to provide a filling space for a bone graft;
4. The intervertebral fusion cage does not affect electromagnetic waves, such as X-rays, MRI scan, CT scan, and the like.

SUMMARY

The disclosure provides an intervertebral fusion device capable of meeting the requirements and adjusting its stiffness to meet the needs of each individual patient, in particular.

The intervertebral fusion device of the disclosure includes a structural ceramic body having a bottom surface, a top surface, a peripheral surface connected between the bottom surface and the top surface, and at least one pore channel penetrating the bottom surface and the top surface. An inner surface of the pore channel is a convex curved surface or the pore channel is a funnel-shaped pore channel. In the pore channel with the convex curved surface, a pore diameter of the pore channel gradually expands from a center of the pore channel to the bottom surface and the top surface. In the funnel-shaped pore channel, a pore diameter of the pore channel gradually expands from the bottom surface to the top surface. The peripheral surface of the structural ceramic body is wavy or zigzag.

In an embodiment of the disclosure, a material of the structural ceramic body includes zirconia ($ZrO_2$), aluminum oxide ($Al_2O_3$), cerium oxide ($CeO_2$), yttrium oxide ($Y_2O_3$), magnesium oxide (MgO), titanium oxide ($TiO_2$), silicon oxide ($SiO_2$), zinc oxide (ZnO), bioglass, silicon nitride, silicon carbide, or a composite material thereof.

In an embodiment of the disclosure, a material of the structural ceramic body includes yttria-tetragonal zirconia polycrystal (Y-TZP), ceria-tetragonal zirconia polycrystal (Ce-TZP), a composite material of yttria-tetragonal zirconia polycrystal and aluminum oxide (Y-TZP/Al2O3) or a composite material of ceria-tetragonal zirconia polycrystal and aluminum oxide (Ce-TZP/Al2O3).

In an embodiment of the disclosure, the bottom surface and the top surface of the structural ceramic body are parallel to each other.

In an embodiment of the disclosure, the bottom surface and the top surface of the structural ceramic body are not parallel to each other.

In an embodiment of the disclosure, the structural ceramic body has a thin side and a thick side. An average diameter of the pore channel closer to the thin side is smaller, and an average diameter of the pore channel closer to the thick side is larger.

In an embodiment of the disclosure, the corners of the peripheral surface to the top surface and to the bottom surface are round corners, and the corners of the inner surface of the pore channel to the top surface and to the bottom surface are also round corners.

In an embodiment of the disclosure, the pore channel of the structural ceramic body is filled with a bone graft.

In an embodiment of the disclosure, a total opening area of the pore channels on the top surface accounts for 10% or more of an area fraction of the top surface.

In an embodiment of the disclosure, a total opening area of the pore channels on the top surface accounts for 50% or more of an area fraction of the top surface.

In an embodiment of the disclosure, the peripheral surface of the structural ceramic body is arc-shaped.

In an embodiment of the disclosure, the bottom surface and the top surface of the structural ceramic body are wavy or zigzag.

In an embodiment of the disclosure, the at least one pore channel is a plurality of pore channels, and the plurality of pore channels are uniformly distributed in the structural ceramic body.

Based on the above, in the disclosure, a structural ceramic body is adopted for working as the basic material of the intervertebral fusion device, and a design of at least one pore channel with a specific shape is adopted in the structural ceramic body. Therefore, the stiffness of the intervertebral fusion device can be adjusted to be close to the stiffness of the bone, and according to the needs of each patient, the stiffness of the intervertebral fusion device can be changed or adjusted through the quantity and the size of the pore channels. Meanwhile, the material of the intervertebral fusion device is ceramic, so it is not only harmless to the human body but also strong enough to support the body weight without affecting electromagnetic waves such as X-rays, MRI scan, CT scan, and the like, which contributes to postoperative follow-up checks. Since the peripheral surface of the structural ceramic body of the disclosure is wavy or zigzag, the intervertebral fusion device is prevented from slipping off after being implanted between the vertebrae, and the engagement of the intervertebral fusion device and the vertebrae is increased.

In order to make the aforementioned features and advantages of the invention comprehensible, embodiments accompanied with drawings are described in detail below.

DESCRIPTION OF THE EMBODIMENTS

Figure 1:
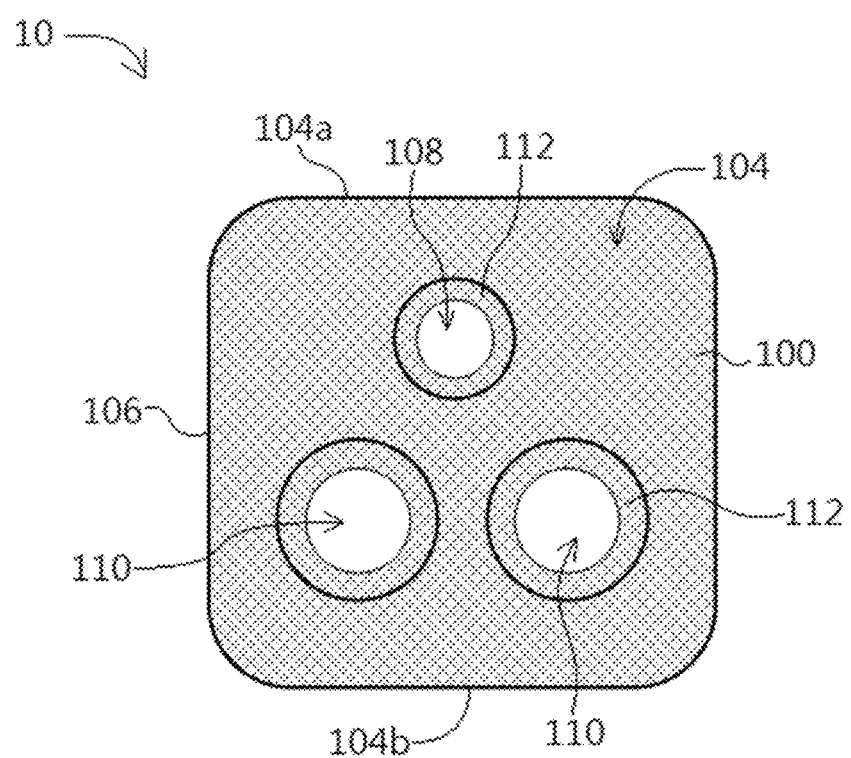
FIG. 1 is a top view of an intervertebral fusion device according to a first embodiment of the disclosure.

Embodiments of the disclosure will be described with reference to the drawings below, but the disclosure may also be implemented in many different forms and should not be interpreted as being limited to the embodiments described below. In the drawings, for the sake of clarity, the sizes of the regions, locations and pore channels and the length and width of the device may not be drawn to actual scale, and for ease of understanding, the same reference numerals may be used to represent the same components in the following.

Figure 2A:
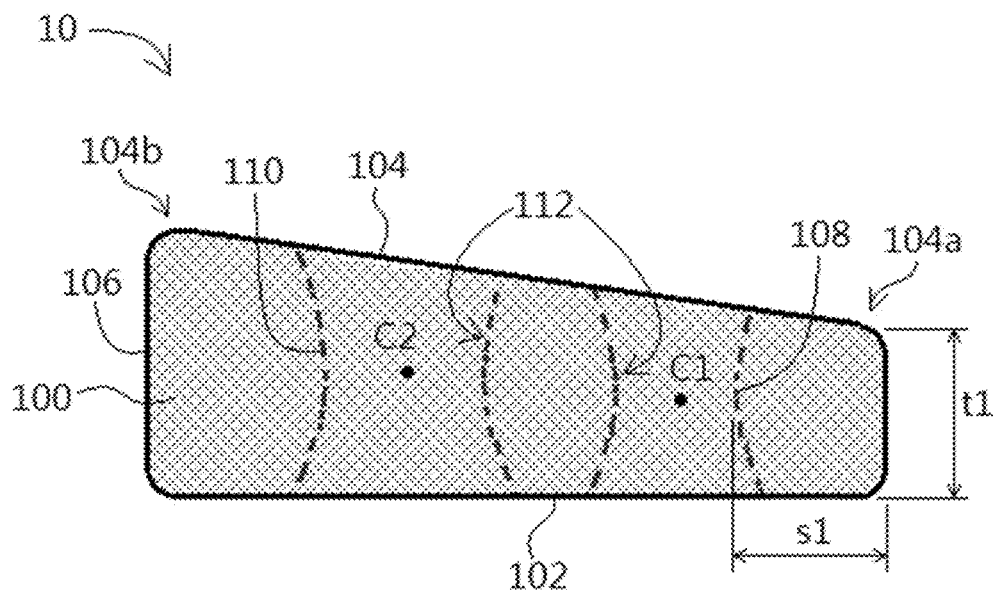
FIG. 2A is a side view of the intervertebral fusion device of FIG. 1.
Figure 2B:
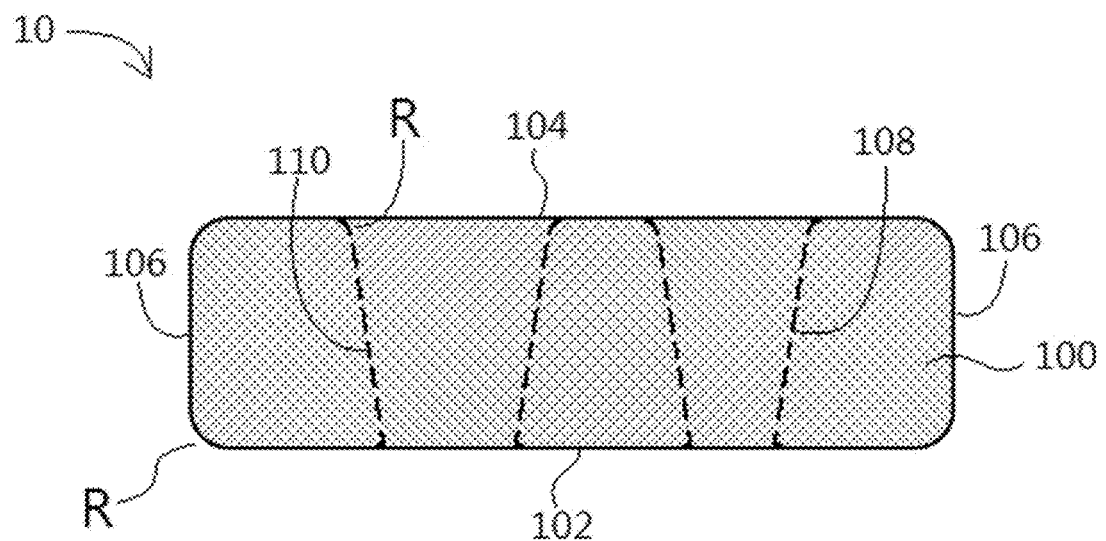
FIG. 2B is another side view of the intervertebral fusion device of FIG. 1.
Figure 2C:
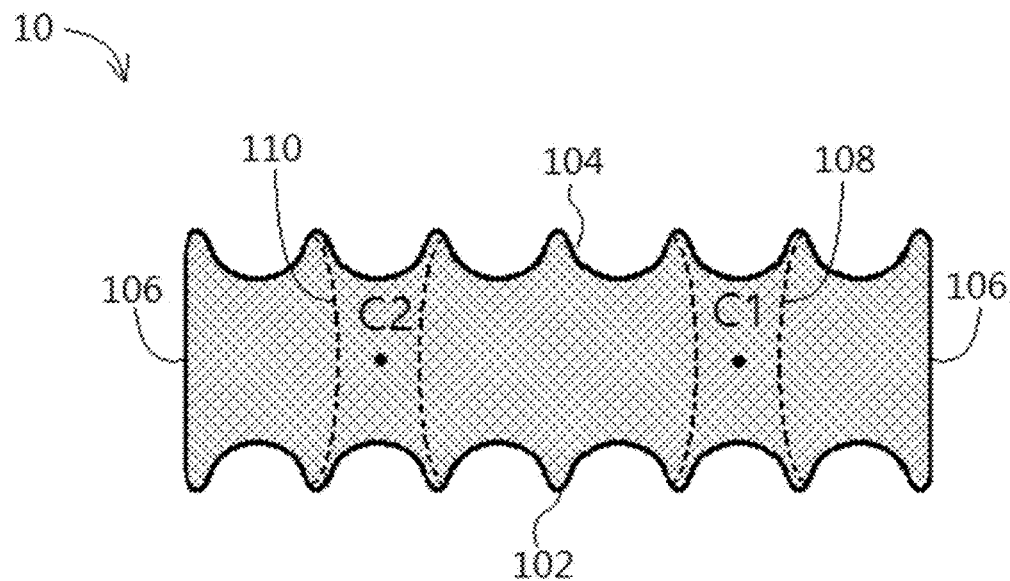
FIG. 2C is still another side view of the intervertebral fusion device of FIG. 1.
Figure 2D:
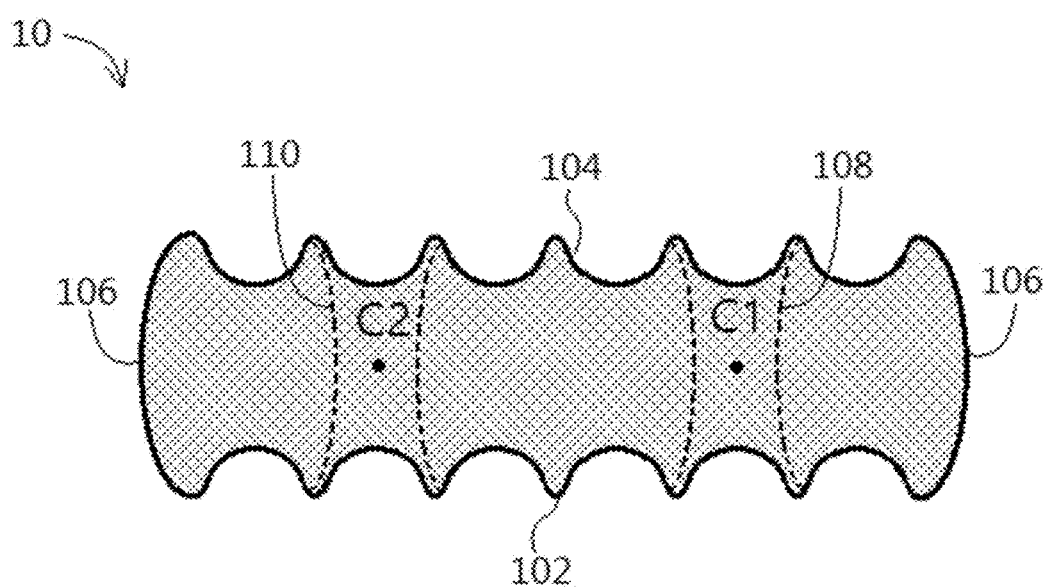
FIG. 2D is yet another side view of the intervertebral fusion device of FIG. 1.

FIG. 1 is a top view of an intervertebral fusion device according to an embodiment of the disclosure, FIG. 2A is a side view of the intervertebral fusion device of FIG. 1, FIG. 2B is a side view of another intervertebral fusion device of FIG. 1, FIG. 2C is a side view of still another intervertebral fusion device of FIG. 1, and FIG. 2D is a side view of yet another intervertebral fusion device of FIG. 1.

Referring to FIG. 1 and FIG. 2A, FIG. 2B, FIG. 2C or FIG. 2D altogether, an intervertebral fusion device 10 of the embodiment includes a structural ceramic body 100. Basically, the material of the structural ceramic body 100 is selected from materials that are harmless to the human body and safe in the human body. Moreover, although bones belong to the internal hard tissues of the human body, the elastic modulus of bone is relatively low. For example, the elastic modulus of cortical bone is about 7 GPa to 30 GPa, so the stiffness of the intervertebral fusion device 10 implanted between the vertebrae and in close contact with the cortical bone should be as close as possible to the cortical bone.

Therefore, the structural ceramic body 100 of the intervertebral fusion device 10 is configured to include a bottom surface 102, a top surface 104, a peripheral surface 106 connected between the bottom surface 102 and the top surface 104. Moreover, multiple pore channels 108 and 110 penetrate the bottom surface 102 and the top surface 104, and the stiffness of the intervertebral fusion device 10 is close to the stiffness of the cortical bone according to the design of the pore channels 108 and 110. To prevent the intervertebral fusion device 10 from slipping off between the vertebrae, the peripheral surface 106 is preferably wavy or zigzag. In addition, to prevent stress concentration, the corners between the bottom surface 102 and the peripheral surface 106 of the structural ceramic body 100 and the corners between the top surface 104 and the peripheral surface 106 can be designed as round corners R, the corners of the peripheral surface 106 can also be designed as round corners R, and the corners of each pore channel 108 and 110 at the openings of the bottom surface 102 and the top surface 104 are also round corners R. Such designs prevent the formation of sharp corners in the entire intervertebral fusion device 10. Without sharp corners, stress concentration is prevented, and the stress uniformity of the intervertebral fusion device 10 in supporting the body weight is improved.

In an embodiment, the material of the structural ceramic body 100 may include ceramic materials, such as zirconia ($ZrO_2$), aluminum oxide ($Al_2O_3$), cerium oxide ($CeO_2$), yttrium oxide ($Y_2O_3$), magnesium oxide (MgO), titanium oxide ($TiO_2$), silicon oxide ($SiO_2$), zinc oxide (ZnO), bioglass, silicon nitride, silicon carbide, and a composite material thereof. To adjust the stiffness of the structural ceramic body 100 for meeting the needs of each patient and for supporting the weight of the human body, the material of the structural ceramic body 100 can be. for example, yttria-tetragonal zirconia polycrystal (Y-TZP), ceria-tetragonal zirconia polycrystal (Ce-TZP), a composite material of yttria-tetragonal zirconia polycrystal (Y-TZP) and aluminum oxide ($Al_2O_3$), or a composite material of ceria-tetragonal zirconia polycrystal (Ce-TZP) and aluminum oxide ($Al_2O_3$).

As for the detailed design of the pore channels 108 and 110, the upper and lower stiffness limits of the structural ceramic body 100 can be estimated first according to the following mathematical formulae (from C L Hsieh, W H Tuan, T T Wu, Elastic behaviour of a model two-phase material, j. European Ceram. Soc., Vol. 24, page 3789-3793, 2004):

1. The upper stiffness limit of the structural ceramic body

The stiffness of the structural ceramic body=(the volume fraction of the ceramic)×(the stiffness of the ceramic)+(the volume fraction of the pore channel)×(the stiffness of the air)   Formula (1).

Since the stiffness of air is zero, formula (1) can be simplified as:

The stiffness of the structural ceramic body=(the volume fraction of the ceramic)×(the stiffness of the ceramic)   Formula (2).

2. The lower stiffness limit of the structural ceramic body

1/(the stiffness of the structural ceramic body)=(the volume fraction of the ceramic)/(the stiffness of the ceramic)+(the volume fraction of the pore channel)/(the stiffness of the air)   Formula (3).

Since the stiffness of air is zero, the value cannot be obtained from the formula (3). The lower stiffness limit of the structural ceramic body can be estimated by using an extremely low value of 0.01 GPa as the stiffness of air.

According to formula (2) and formula (3), the stiffness of the structural ceramic body 100 may rapidly decrease as the number of pore channels increases, so the number of pore channels can also be one or plurality as the case of uniformly distributed pore channels 108 and 110 adopted in the structural ceramic body 100. For example, when the total opening area fraction of the pore channels 108 and 110 is 10%, the stiffness of the structural ceramic body 100 can be reduced by 10% or more. Therefore, changing the quantity and the diameter of the pore channels 108 and 110 can adjust the stiffness of the structural ceramic body 100.

In addition to stiffness, the intervertebral fusion device 10 should be strong enough to support the weight of the human body. Especially when a person is running or jumping, the intervertebral fusion device 10 must be strong to withstand the impact. For the intervertebral fusion device 10, the external load is mainly along the direction of the spine, so the central axis of each pore channel 108 and 110 is preferably parallel to the extending direction of the spine.

Next, referring to FIG. 2A, the top surface is not parallel to the bottom surface. The top surface 104 is inclined. Inner surfaces 112 of the pore channels 108 and 110 may be convex curved surfaces. Moreover, the pore diameter of the pore channel 108 gradually expands from the center C1 of the pore channel 108 to the bottom surface 102 and the top surface 104; the pore diameter of each pore channel 110 also gradually expands from the center C2 of the pore channel 110 to the bottom surface 102 and the top surface 104. Moreover, to prevent stress concentration, the corners of the inner surfaces 112 of the pore channels 108 and 110 and the top surface 104 and the bottom surface 102 may also be round corners. Since the bottom surface 102 and the top surface 104 are in contact with the vertebrae, the actual contact area of the structural ceramic body 100 with the vertebrae is relatively small, which reduces the effective stiffness of the structural ceramic body 100. For example, the total opening area of the pore channels 108 and 110 on the top surface 104 accounts for 10% or more of the area fraction of the top surface 104, such as 10%, 20%, 30%, 40%, 50%, 60%, and the like; preferably more than 50%.

Moreover, as described, the elastic modulus can be adjusted by changing the quantity and the diameter of the pore channels 108 and 110, so the stiffness of the structural ceramic body 100 can be further reduced.

Moreover, the pore diameters of the pore channels 108 and 110 are smaller at the centers C1 and C2, which can further increase the ability of the intervertebral fusion device 10 to support external loads. Moreover, to match the shape of the vertebrae, the intervertebral fusion device 10 does not have the same thickness, so a thin side 104a of the top surface 104 is a thinner portion of the structural ceramic body 100, and a thick side 104b is a thicker portion of the structural ceramic body 100. Therefore, in the pore channels 108 and 110, the average diameter of the pore channel 108 closer to the thin side 104a of the top surface 104 is smaller, and the average diameter of the pore channel 110 closer to the thick side 104b of the top surface 104 is greater. For example, the average diameter of the pore channel 108 is smaller than the average diameter of the pore channel 110, and the quantity of the pore channels 108 may also be less than the quantity of the pore channels 110. In addition, regarding the structural strength, the distance s1 between the portion of inner surface 112 at the center C1 of the pore channel 108 and the portion at the thinnest point of the thin side 104a is preferably larger than the thinnest thickness t1 of the structural ceramic body 100.

In another embodiment, referring to FIG. 2B, the bottom surface 102 and the top surface 104 of the structured ceramic body 100 are parallel to each other, so the structure of FIG. 2B can have no thick side and thin side. The pore channels 108 and 110 may also be funnel-shaped, and the pore diameters of the pore channels 108 and 110 both gradually expand from the bottom surface 102 to the top surface 104. With the disposition of the funnel-shaped pore channel, not only the contact area between the top surface 104 of the structural ceramic body 100 and the vertebra is reduced, but also the effective stiffness of the structural ceramic body 100 is reduced, and the disposition further contributes to the subsequent unidirectional filling of the bone graft (not shown). Moreover, as described, the elastic modulus can be adjusted by increasing the quantity of the pore channels 108 and 110 and the diameter of the opening, so the stiffness of the structural ceramic body 100 can be further reduced.

In another embodiment, referring to FIG. 2C, the bottom surface 102 and the top surface 104 of the structural ceramic body 100 may also be wavy or zigzag to strengthen the fixation to the upper and lower vertebrae.

In another embodiment, referring to FIG. 2D, the peripheral surface 106 of the structured ceramic body 100 may also be arc-shaped to disperse the stress in the structured ceramic body 100.

In still another embodiment, both the bottom surface 102 and the top surface 104 of the structural ceramic body 100 may be inclined surfaces, and the bottom surface 102 and the top surface 104 are not parallel to each other. For example, the intervertebral fusion device 10 may have a structure similar to that shown in FIG. 2A, but the bottom surface 102 of the structural ceramic body 100 is also inclined and tilted from the thick side 104b toward the thin side 104a. Therefore, the thinnest thickness is less than t1 in FIG. 2A, and the average diameter of the pore channels 108 closer to the thin side 104a is smaller, and the average diameter of the pore channels 110 closer to the thick side 104b is larger. On the other hand, the bottom surface 102 of the structural ceramic body 100 can also be tilted from the thin side 104a toward the thick side 104b to match the curvature of the vertebra. Therefore, the intervertebral fusion device 10 of the disclosure is not limited to the content of the drawings, and changes can also be made to the structure according to requirements.

In the first embodiment, the bone graft (not shown) filled in the pore channels 108 and 110 of the structural ceramic body 100 is an autologous bone graft or a synthetic bone graft, for example. The synthetic bone graft includes but is not limited to hydroxyapatite, and tricalcium phosphate or calcium sulfate or a solid solution thereof or a composite material thereof. The bone graft can be filled into the pore channels 108 and 110 before a surgery so that the bone graft is in close contact with the vertebrae after the surgery and slowly releases ions and substances that assist bone healing to achieve the purpose of bone fusion. For example, the bone graft may contain ions or growth factors to enhance bone healing and bone fusion. For example, strontium ions can enhance bone formation and inhibit bone resorption. The delivery of strontium ions to the vertebrae can be accomplished by using a solid solution of calcium salts and strontium solute. The degradation of the solid solution of calcium salts and strontium solute takes months or even years, so the use of this kind of bone graft can contribute to the stiffness of the vertebrae for a long time. The solid solution of calcium salts and strontium solute can fill the pore channels 108 and 110 in the form of bone graft before the surgery.

Regarding the manufacture of the intervertebral fusion device 10, the following methods can be used, but the disclosure is not limited thereto.

First, in one embodiment, zirconia may be selected as the main raw material of the structural ceramic body 100, and yttrium oxide or cerium oxide may be added to stabilize the crystal phase. To prevent aging in a humid environment (in the human body), the content of the yttrium oxide is preferably 3 mol % or more. For example, the content of yttrium oxide in zirconia may range from 3 mol % to 8 mol %. The content of the cerium oxide is preferably 5 mol % or more. Because the stiffness of alumina is about twice that of zirconia, adding alumina particles can restrain the volume expansion of zirconia, the volume expansion of zirconia due to aging is constrained consequently, and the aging resistance of zirconia is increased. Therefore, based on the total weight of the structural ceramic body 100, the content of alumina is preferably 30 wt % or less, and alumina with the content less than 0.1 wt % can be dissolved into zirconia.

In another embodiment, ceria-tetragonal zirconia polycrystal and aluminum oxide (Ce-TZP/Al2O3) which is resistant to aging, can be used as the material of the structural ceramic body 100, and the raw material contains 70 vol % of Ce-TZP (ZrO2-10 mol % CeO2) and 30 vol % of Al2O3.

In yet another embodiment, the raw material of the structural ceramic body 100 may be a composite material including 67.9 wt % of ZrO2, 10.6 wt % of CeO2, and 21.5 wt % of Al2O3 and less than 0.1 wt % of other oxides (MgO and/or TiO2).

Then, the raw materials are made into green bodies, and the forming techniques include but are not limited to die-pressing, isostatic pressing, slip casting, injection molding, and the like. Subsequently, a debinding treatment is performed at a temperature lower than 600° C. to remove all the binders in the green body, and the storage time of the green body is therefore increased.

When the size and shape of the intervertebral fusion device 10 required by the patient is acquired, a milling machine (e.g., a five-axis milling machine) can be used to process the green body into the shape of the intervertebral fusion device 10. The size and the shape of the intervertebral fusion device 10 required by the patient can be obtained by X-ray, MRI scan, or CT scan before operation. The scan file can be converted into a digital data file and then sent to the milling machine for subsequent processing.

Next, a sintering process is performed. During the sintering process, the green body is expected to undergo linear shrinkage of about 10% to 20%, so the size of the green body is larger than that of the sintered intervertebral fusion device 10. Since the shrinkage of the green body is relatively uniform in each direction, once the size and shape of the final intervertebral fusion device 10 are determined, the size of the green body can be estimated.

Figure 3:
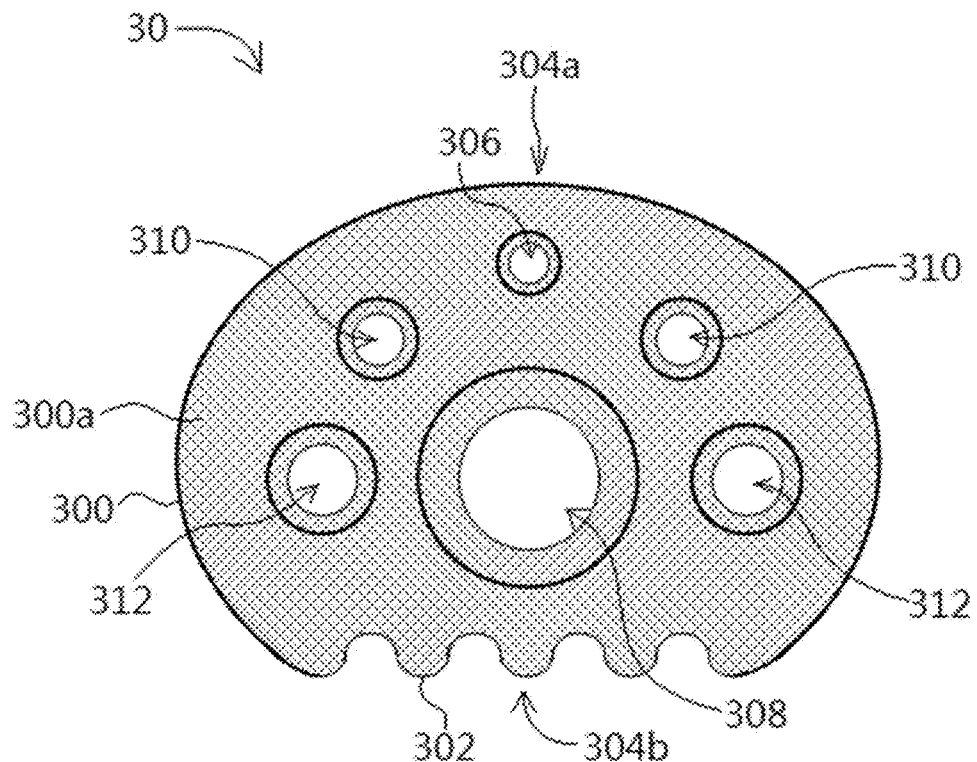
FIG. 3 is a top view of an intervertebral fusion device according to a second embodiment of the disclosure.

FIG. 3 is a top view of an intervertebral fusion device according to a second embodiment of the disclosure. The technical terms of the first embodiment are used to illustrate the same components, and for the description of the same components, refer to the relevant description of the first embodiment, which is not iterated herein.

In FIG. 3, a peripheral surface 302 of a structural ceramic body 300 of a intervertebral fusion device 30 is wavy or zigzag, which achieves the effect of increasing the contact area with the surrounding tissues of the human body, so it is not easy for the intervertebral fusion device 30 to slip off after being implanted between the vertebrae. Moreover, the top surface 300a and the bottom surface (not shown) of the structural ceramic body 300 may also be wavy to strengthen the fixation of the upper and lower vertebrae. A thin side 304a is the thinner portion of the structural ceramic body 300, and a thick side 304b is the thicker portion of the structural ceramic body 300. Therefore, the size of a pore channel 306 closest to the thin side 304a is the smallest, the size of a central pore channel 308 is the largest, the size of pore channel 310 disposed between the pore channels 306 and 308 ranges in between, and the size of pore channels 312 close to the thick side 304b of two sides of the pore channel 308 is slightly smaller than the size of the central pore channel 308 but larger than the size of the pore channel 310. Moreover, to prevent stress concentration at any point, the corners of the intervertebral fusion device 30 are round corners over the entire circumference (the peripheral surface 302), and the corners of the openings on the top surface 300a and the bottom surface (not shown) are also round corners.

Figure 4:
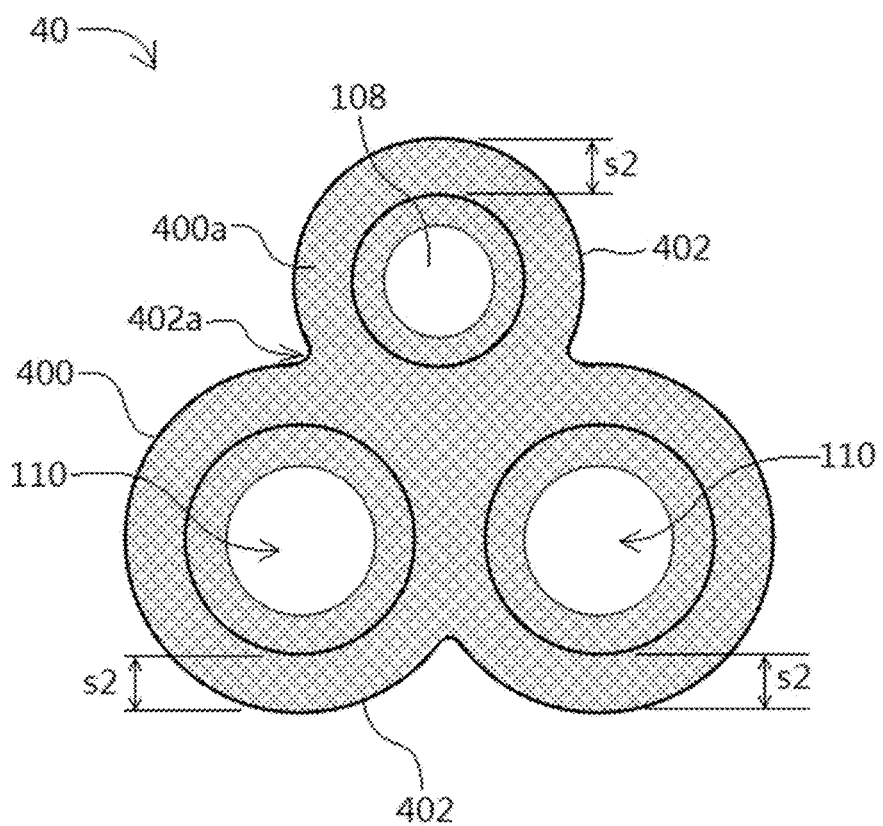
FIG. 4 is a top view of an intervertebral fusion device according to a third embodiment of the disclosure.

FIG. 4 is a top view of an intervertebral fusion device according to a third embodiment of the disclosure. The technical terms of the first embodiment are used to illustrate the same components, and for the description of the same components, refer to the relevant description of the first embodiment, which is not iterated herein.

In FIG. 4, distances s2 between a peripheral surface 402 of a structural ceramic body 400 of an intervertebral fusion device 40 and the closest pore channels 108 and 110 are the same, and the corners of the peripheral surface 402 still maintain the shape of round corner. That is, a corner 402a of the peripheral surface 402 is also a round corner. Moreover, to prevent the intervertebral fusion device 40 from slipping off after being implanted between the vertebrae and to increase the engagement between the intervertebral fusion device 40 and the vertebra, the peripheral surface 402 of the intervertebral fusion device 40 can be designed to be wavy (or zigzag) as shown in FIG. 4. Moreover, the top surface 400a and the bottom surface (not shown) of the intervertebral fusion device 40 may also be wavy to strengthen the fixation to the upper and lower vertebrae.

Several simulation experiments are illustrated below to verify the efficacy of the disclosure, but the disclosure is not limited to the following content. Since the wavy and zigzag top and bottom surfaces are fixed into the upper and lower vertebrae after implantation. The structural body is the part under the weight of human body. Therefore, the structural body under load is simulated.

<Comparison Group 1>

Figure 5:
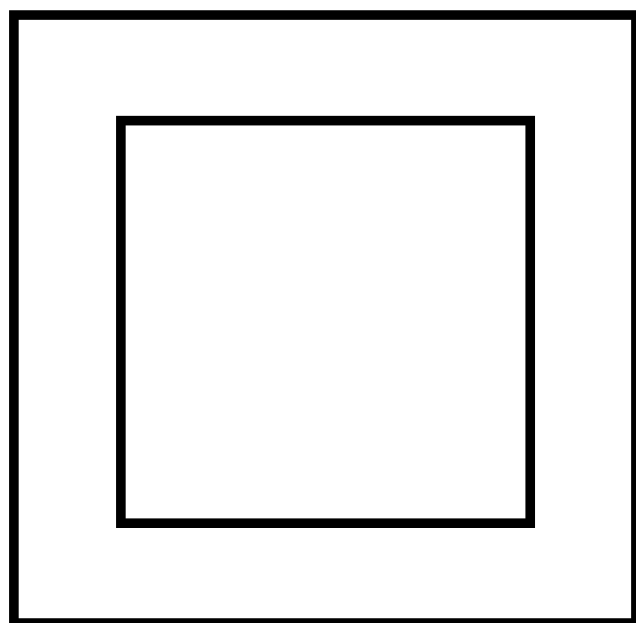
FIG. 5 is a top view of the structure of the comparison group 1.
Figure 5:

Structure: A square structure has a square hole in the middle as shown in the top view in FIG. 5. The top and bottom surfaces of the square structure are both 12 mm×12 mm, and the thickness is 9 mm; the size of the square hole is 8 mm×8 mm (the inner surface is a flat surface). The top surface area of the square structure is 80 mm$^2$; the pore channel opening area accounts for 44% of the top surface area.

Simulation method: A simulation structure is used to calculate and analyze the structure, a uniaxial load of 30,000N is applied to the top surface, and then the largest stress and average stress that appear during the compression process are calculated.

Simulation results: The largest stress is 805 MPa and the average stress is 361 MPa. The largest stress appears in the four outer corners of the bottom of the square structure, indicating that the stress is concentrated in the sharp-angle part.

<Comparison Group 2>

Figure 6:
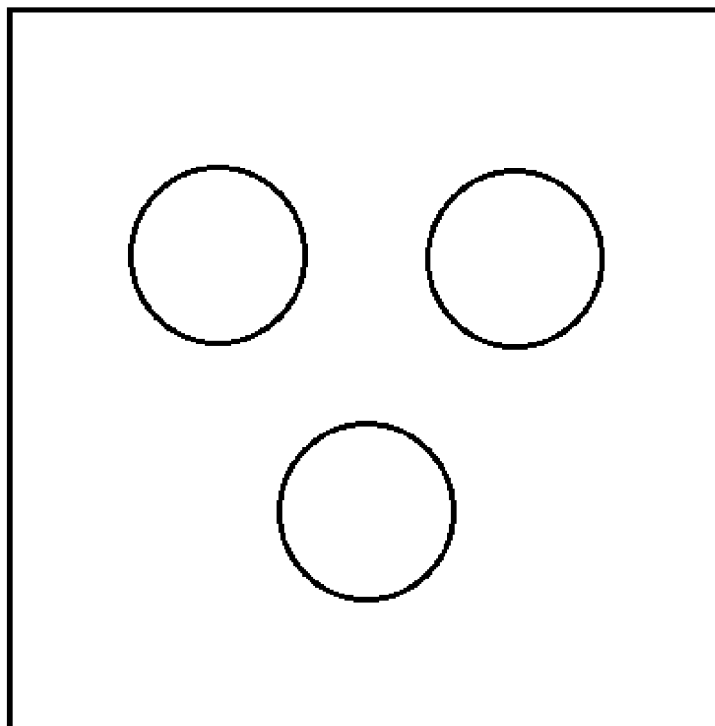
FIG. 6 is a top view of the structure of the comparison group 2.
Figure 6:
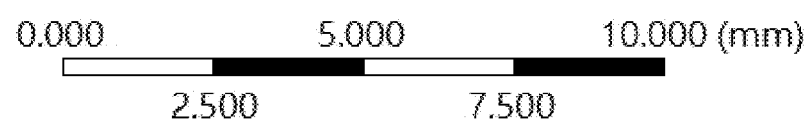

Structure: A square structure has three circular pore channels as shown in the top view in FIG. 6. The top and bottom surfaces of the square structure are both 12 mm×12 mm, and the thickness is 9 mm; the diameters of both circular pore channels are 3 mm (the inner surface is a flat surface). The top surface area of the square structure is 123 mm$^2$; the total opening area of the pore channels accounts for 15% of the top surface area.

Simulation method: A simulation structure is used to calculate and analyze the structure, a uniaxial load of 30,000N is applied to the top surface, and then the largest stress and average stress that appear during the simulation compression process are calculated.

Simulation results: The largest stress is 552 MPa, and the average stress is 233 MPa. This comparison group shows that when the area of the structure increases, the largest stress and the average stress are decreased. However, the largest stress still appears in the four outer corners of the bottom of the square structure, indicating that the stress concentration is still in the sharp-angle part.

Experimental Example 1

Figure 7:
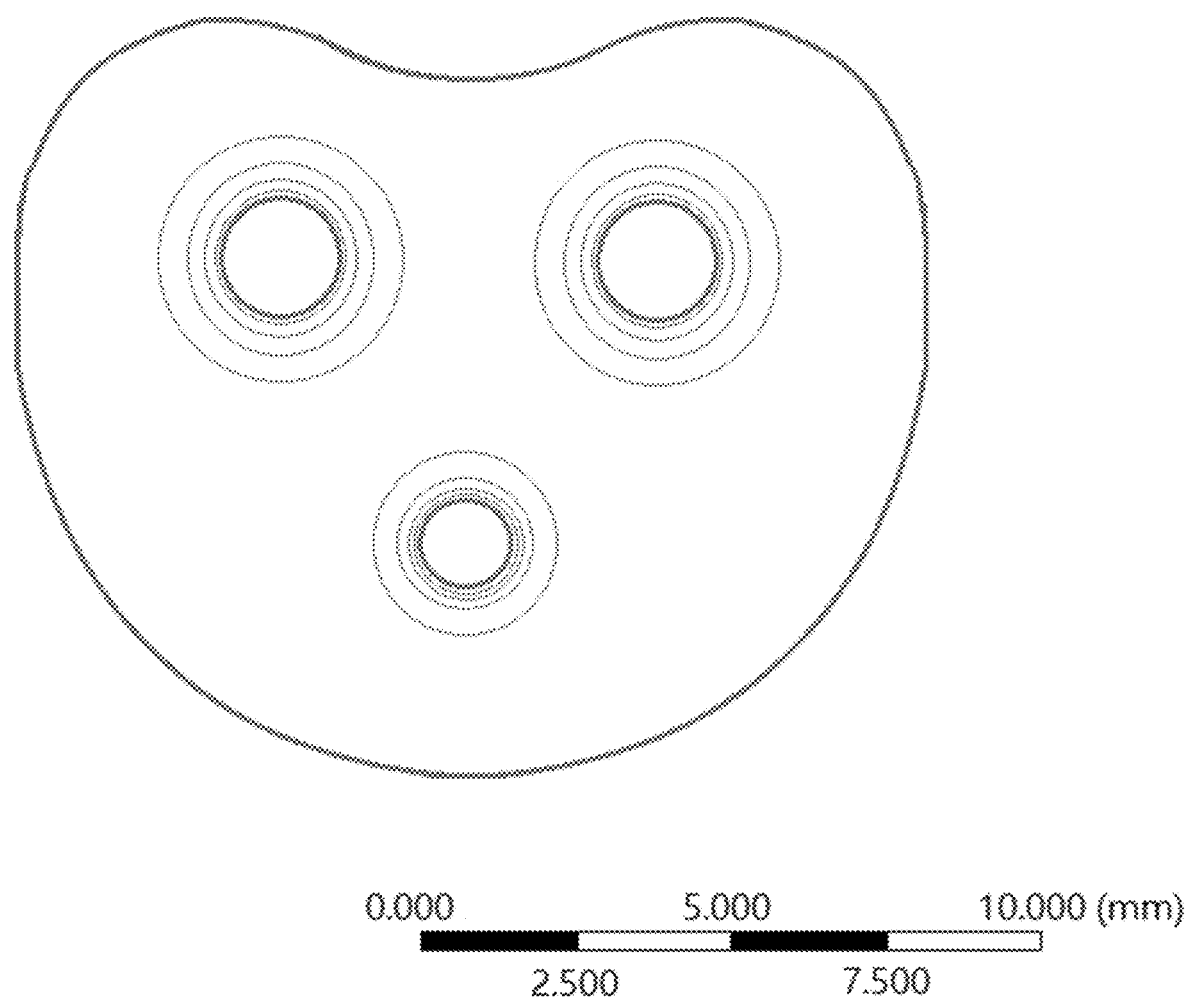
FIG. 7 is a top view of the structure of experimental example 1.

Structure: A wavy structure has three circular pore channels having a convex curved surface as shown in the top view in FIG. 7, and the outer diameters of the two larger pore channels are 4 mm, and the center diameters are 2 mm. The outer diameter of the small pore channel is 3 mm, the center diameter is 1.5 mm, and the thickness is 9 mm; the top surface area of the structure is 73 mm$^2$; the total opening area of the pore channels accounts for 42% of the top surface area. In this structure, all corners are round corners.

Simulation method: A simulation structure is used to calculate and analyze the structure, a uniaxial load of 30,000N is applied to the top surface, and then the largest stress and average stress that appear during the compression process are calculated.

Simulation results: The largest stress is 568 MPa, and the average stress is 255 MPa. Compared to comparison group 2, even if the top surface area is reduced from 123 mm$^2$ to 73 mm$^2$, the largest stress and average stress hardly increase. According to the simulation results, there should be no sharp angles anywhere in the structure so that the stress concentration can be reduced. Moreover, the inside of the pore channel protrudes inward, so the internal stress inside the pore channel is significantly lower, and therefore the opening area can be enlarged, the contact area with the vertebrae can be reduced, and the stiffness of the structure can be effectively reduced. Moreover, with the design of the inside of the pore channel protruding inward, the chance of internal stress concentration is reduced, the sharp angle of the surface of the pore channel is reduced, and the chance of stress concentration is further reduced.

Experimental Example 2

Figure 8:
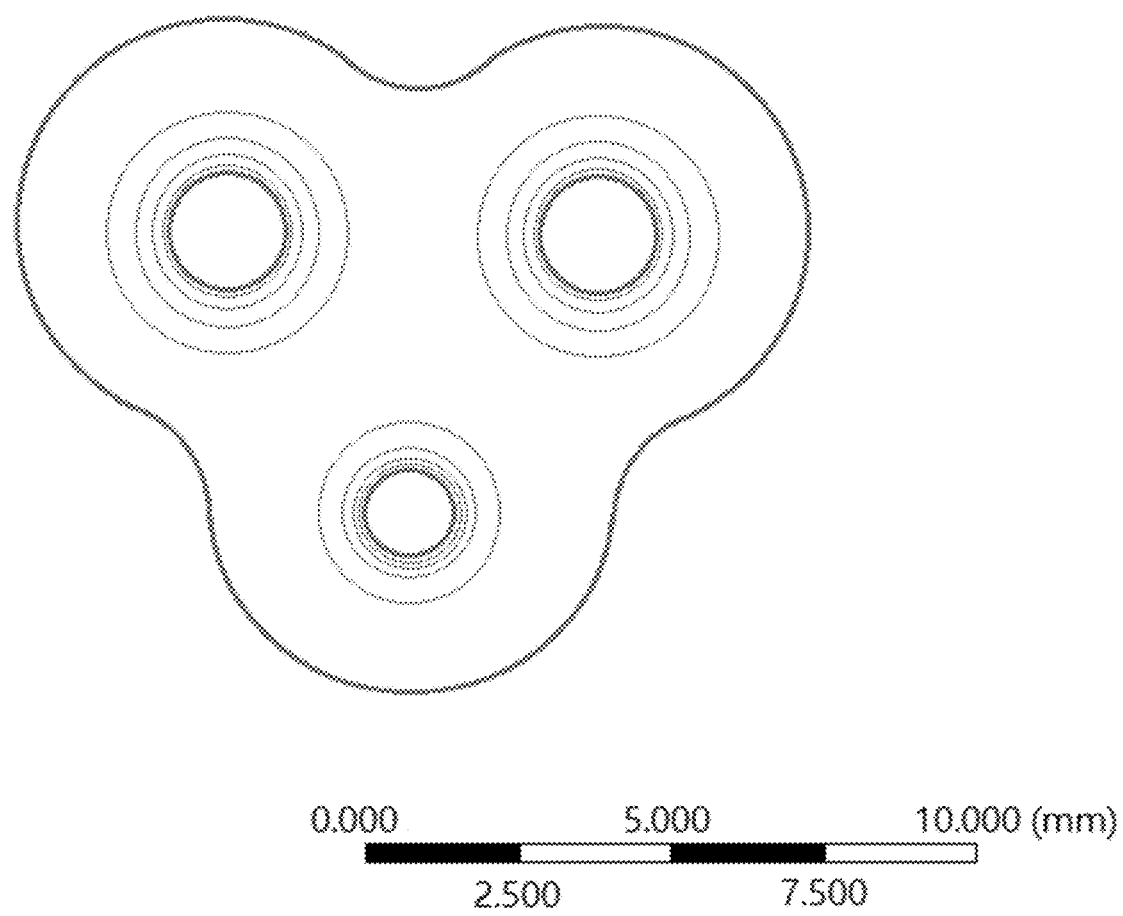
FIG. 8 is a top view of the structure of experimental example 2.

Structure: A structure with a wavy exterior has three circular pore channels having an inner convex surface as shown in the top view in FIG. 8, and the outer diameters of the two larger pore channels are 4 mm and the center diameter is 2 mm, and the outer diameter of the smaller pore channel is 3 mm and the center diameter is 1.5 mm, the thickness is 9 mm; the top surface area of the structure is only 56 mm$^2$; the total opening area of the pore channels accounts for about 54% of the top surface area. In this structure, all corners are round corners.

Simulation method: A simulation structure is used to calculate and analyze the structure, a uniaxial load of 30,000N is applied to the top surface, and then the largest stress and average stress that appear during the compression process are calculated.

Simulation results: The largest stress is 738 MPa, and the average stress is 303 MPa. Compared to comparison group 2, even if the top surface area is greatly reduced from 123 mm$^2$ to 56 mm$^2$, the average stress increases in a limited manner. According to the simulation results, there should be no sharp angles anywhere in the structure so that the stress concentration can be reduced. Moreover, the inside of the pore channel protrudes inward, so the internal stress inside the pore channel is significantly lower, and with the wavy design, the area of the top and bottom surfaces can be reduced, the contact area with the vertebrae can be reduced, and the stiffness of the structure can be reduced effectively. Moreover, with the design of the inside of the pore channel protruding inward, the chance of internal stress concentration is reduced, the sharp angle of the surface of the pore channel is reduced, and the chance of stress concentration is further reduced.

The analyses of the four groups illustrate:
A. There should be no sharp angles at any corner of the structure to reduce stress concentration.
B. As the area of the top and bottom surfaces of the structure gets smaller, the stiffness of the structure can be reduced. Meanwhile, with the design of the inside of the pore channel protruding inward, the chance of internal stress concentration is reduced.

Based on the above, the disclosure provides a design of an intervertebral fusion device adapted for replacing damaged discs in the cervical or lumbar spine, and the stiffness of the intervertebral fusion device can be adjusted to meet the needs of each patient. Meanwhile, the material of the intervertebral fusion device is ceramic, so it is not only harmless to the human body but also strong enough to support the body weight without affecting electromagnetic waves, such as X-rays, MRI scan, CT scan, and the like, which contributes to the subsequent follow-up checks.

Although the disclosure has been described with reference to the above embodiments, they are not intended to limit the disclosure. It will be apparent to one of ordinary skill in the art that modifications and changes to the described embodiments may be made without departing from the spirit and the scope of the disclosure. Accordingly, the scope of the disclosure will be defined by the attached claims and their equivalents and not by the above detailed descriptions.

What is claimed is:

1. An intervertebral fusion device, comprising:
a structural ceramic body comprising a bottom surface, a top surface, a peripheral surface connected between the bottom surface and the top surface, and at least one pore channel penetrating the bottom surface and the top surface, wherein a number of the at least one pore channel is 3 or less, and a total opening area of the at least one pore channel on the top surface accounts for 20% or more of an area fraction of the top surface,
wherein an inner surface of the pore channel is a convex curved surface, a plurality of corners of the peripheral surface to the top surface and to the bottom surface are round corners, and a plurality of corners of the inner surface of the pore channel to the top surface and to the bottom surface are also round corners,
in the pore channel with the convex curved surface, a pore diameter of the pore channel gradually expands from a center of the pore channel to the bottom surface and the top surface, and
the peripheral surface is wavy or zigzag.

2. The intervertebral fusion device according to claim 1, a material of the structural ceramic body comprises zirconia (ZrO2), aluminum oxide (Al2O3), cerium oxide (CeO2), yttrium oxide (Y2O3), magnesium oxide (MgO), titanium oxide (TiO2), silicon oxide (SiO2), zinc oxide (ZnO), bioglass, silicon nitride, silicon carbide, or a composite material thereof.

3. The intervertebral fusion device according to claim 1, a material of the structural ceramic body comprises yttria-tetragonal zirconia polycrystal (Y-TZP), ceria-tetragonal zirconia polycrystal (Ce-TZP), a composite material of yttria-tetragonal zirconia polycrystal and aluminum oxide (Y-TZP/Al2O3) or a composite material of ceria-tetragonal zirconia polycrystal and aluminum oxide (Ce-TZP/Al2O3).

4. The intervertebral fusion device according to claim 1, wherein the bottom surface and the top surface of the structural ceramic body are parallel to each other.

5. The intervertebral fusion device according to claim 1, wherein the bottom surface and the top surface are not parallel to each other.

6. The intervertebral fusion device according to claim 5, wherein the structural ceramic body comprises a thin side and a thick side, an average diameter of the pore channel closer to the thin side is smaller, and an average diameter of the pore channel closer to the thick side is larger.

7. The intervertebral fusion device according to claim 1, wherein the peripheral surface is arc-shaped.

8. The intervertebral fusion device according to claim 1, wherein the pore channel of the structural ceramic body is filled with a bone graft.

9. The intervertebral fusion device according to claim 1, wherein the total opening area of the pore channels on the top surface accounts for 50% or more of the area fraction of the top surface.

10. The intervertebral fusion device according to claim 1, wherein both the bottom surface and the top surface of the structural ceramic body are wavy or zigzag.

11. The intervertebral fusion device according to claim 1, wherein the at least one pore channel is a plurality of pore channels, and the plurality of pore channels are uniformly distributed in the structural ceramic body.

* * * * *